(12) United States Patent
Klaiman

(10) Patent No.: US 11,385,179 B2
(45) Date of Patent: Jul. 12, 2022

(54) TARGET MOLECULE DENSITY DETERMINATION IN A FLUORESCENCE IMAGE

(71) Applicant: HOFFMANN-LA ROCHE INC., Little Falls, NJ (US)

(72) Inventor: Eldad Klaiman, Penzberg (DE)

(73) Assignee: HOFFMANN-LA ROCHE, INC., Little Falls, NJ (US)

( * ) Notice: Subject to any disclaimer, the term of this patent is extended or adjusted under 35 U.S.C. 154(b) by 139 days.

(21) Appl. No.: 16/500,869

(22) PCT Filed: Apr. 13, 2018

(86) PCT No.: PCT/EP2018/059528
§ 371 (c)(1),
(2) Date: Oct. 4, 2019

(87) PCT Pub. No.: WO2018/189370
PCT Pub. Date: Oct. 18, 2018

(65) Prior Publication Data
US 2020/0033267 A1 Jan. 30, 2020

(30) Foreign Application Priority Data

Apr. 13, 2017 (EP) ..................................... 17166661

(51) Int. Cl.
*G06K 9/00* (2022.01)
*G01N 21/64* (2006.01)
(Continued)

(52) U.S. Cl.
CPC ..... *G01N 21/6458* (2013.01); *G01N 21/6486* (2013.01); *G01N 33/5005* (2013.01); *G06T 7/0012* (2013.01)

(58) Field of Classification Search
None
See application file for complete search history.

(56) References Cited

U.S. PATENT DOCUMENTS

| 5,196,306 A | 3/1993 | Bobrow et al. |
| 5,583,001 A | 12/1996 | Bobrow et al. |

(Continued)

FOREIGN PATENT DOCUMENTS

| CN | 1234114 A | 11/1999 |
| CN | 101688838 A | 3/2010 |

(Continued)

OTHER PUBLICATIONS

International Preliminary Report on Patentability dated Oct. 24, 2019, issued in corresponding PCT Application No. PCT/EP2018/059528.

(Continued)

*Primary Examiner* — Wei Wen Yang
(74) *Attorney, Agent, or Firm* — Harness, Dickey & Pierce, P.L.C.

(57) ABSTRACT

The method includes receiving a digital image of a slide, the slide including the tissue sample, a target dot and a fluoro dot. The digital image includes intensity values of the tissue sample, the target dot and the fluoro dot. The method further includes receiving pixel intensities of the fluoro dot depicted in the image; pixel intensities of the target dot depicted in the image; pixel intensities of an area of the tissue sample depicted in the image; fluorescence-inducing molecule density information indicative of the known density of the fluorescence-inducing molecules in the fluoro dot; target molecule density information indicative of the known density of the target molecules in the target dot; and computing the density of target molecules in the area of the tissue sample as a function of the received pixel intensities and the received molecule density information.

19 Claims, 3 Drawing Sheets

(51) Int. Cl.
*G01N 33/50* (2006.01)
*G06T 7/00* (2017.01)

(56) References Cited

U.S. PATENT DOCUMENTS

| | | | |
|---|---|---|---|
| 5,731,158 | A | 3/1998 | Bobrow et al. |
| 6,471,916 | B1 | 10/2002 | Noblett |
| 9,395,283 | B1 | 7/2016 | Chan et al. |
| 9,396,283 | B2 | 7/2016 | Miranker et al. |
| 2003/0015668 | A1 | 1/2003 | Montagu |
| 2004/0060987 | A1 | 4/2004 | Green |
| 2012/0262564 | A1* | 10/2012 | Marcelpoil ........... G06T 7/0012 348/79 |
| 2013/0338014 | A1 | 12/2013 | McDonough et al. |
| 2019/0271647 | A1* | 9/2019 | Grabmayr .......... G01N 21/6428 |

FOREIGN PATENT DOCUMENTS

| | | |
|---|---|---|
| CN | 103620413 A | 3/2014 |
| CN | 104634962 A | 5/2015 |
| EP | 1774292 B1 | 4/2016 |
| WO | WO-00/51058 A1 | 8/2000 |
| WO | WO-01/35074 A1 | 5/2001 |
| WO | WO-01/59503 A2 | 8/2001 |

OTHER PUBLICATIONS

International Search Report PCT/ISA/210 for International Application No. PCT/EP2018/059528 filed Apr. 13, 2018.
Written Opinion of the International Searching Authority PCT/ISA/237 for International Application No. PCT/EP2018/059528 filed Apr. 13, 2018.
Peluso, "Optimizing antibody immobilization strategies for the construction of protein microarrays" . 2003, Analytical Biochemistry, vol. 312, p. 113-124, Academic Press.
Zhu et al., "Analysis of yeast protein kinases using protein chips," 2000, Nature Genetics, vol. 26, p. 283-289.
MacBeath et al., "Printing Proteins as Microarrays for High-Throughput Function Determination," 2000, Science, vol. 289, p. 1760-1763.
Stillman et al., "Fast™ Slides" a (Novel Surface of Microarrays, 2000, Biotechniques, vol. 29, p. 630-635.
Guilleaume et al., "*Systematic comparison of surface coatings for protein microarrays*," 2005, Proteomics, vol. 5, p. 4705-4712 4705, WILEY-VCH Verlag GmbH & Co, KGaA, Weinheirn.
Roth et al., "Enzyme-Based Fluorescence Amplification for Immunohistochemistry and in Situ Hybridization," 2005, Molecular Morphology in Human Tissues, CRC Press.
Roth et al, "Cell and Tissue Imaging Techniques," 2005, Translational And Experimental Clinical Research, Chapter 36.
Bobrow et al., "The use of catalyzed reporter deposition as a means of signal amplification in a variety of formats," 1992, Journal of Immunological Methods, vol. 150, p. 145-149, Etsevier Science Publishers B.V.
Adams, "Biotin Amplification of Biotin and Horseradish Peroxidase Signals in Histochemical Stains," 1992, The Journal of Histochemistry and Cytochemistry, vol, 40, No. 10, p. 1457-1463, The Histocherni-cal Society, Inc.
Shindler, Double Immunofluorescent Staining Using Two Unconjugated Primary Antisera Raised in the Same Species, 1996, The Journal of Histochemistry and Cytochemistry, vol. 44, No. 11, p. 1331-1335, The Histochemical Society, Inc.
Office Action for Corresponding Japanese Patent Application No. 2019-553845 dated Feb. 8, 2022 and English Translation thereof.
Office Action for Corresponding Chinese Patent Application No. 201880024609.9 dated Dec. 30, 2021 and English Translation thereof.

* cited by examiner

TARGET MOLECULE DENSITY DETERMINATION IN A FLUORESCENCE IMAGE

CROSS-REFERENCE TO RELATED APPLICATIONS

This application is a national phase under 35 U.S.C. § 371 of PCT International Application No. PCT/EP2018/059528 which has an International filing date of Apr. 13, 2018, which claims priority to European patent application number EP 17166661.3 filed Apr. 13, 2017.

FIELD OF THE INVENTION

The invention relates to the field of image analysis, and more particularly to the field of fluorescence image-based quantification of target molecules.

BACKGROUND AND RELATED ART

Fluorescence microscopes are commonly used for studying particular cells which have been labeled with fluorescence-labeled antibodies or other fluorescence labeled proteins in order to detect the occurrence and, at least roughly, the quantity of a particular molecule of interest. For example, fluorescence microscope images are often generated and analyzed in order to determine if and to what amount a particular biomarker (being an indicator of a physiological state, e.g. a disease, in particular a cancer or cancer sub-type) is present in a cell.

Typically, fluorescence intensity and biomarker expression are positively correlated and the intensity of a fluorescence signal is used as an indicator for the amount of the biomarker.

However, due to various instrumental factors, the same sample imaged on two microscopes or even on the same microscope at different times may produce highly divergent readings. Second, the ratio of antibody molecules which bind to the biomarker and/or the ratio of fluorescent dye molecules that bind to an antibody molecule may strongly depend on process parameters of the staining process (such as temperature, incubation time, buffer, type of fluorophore molecule, etc). Therefore, the fluorescence intensity signal in fluorescence images does typically not allow an accurate determination of the number of biomarker molecules expressed in a cell and thus does not allow to accurately compare expression levels of two tissue samples having been stained in different staining procedures by means of fluorescence microscopy.

U.S. Pat. No. 9,395,283 B1 describes the generation of homogeneous cell blocks (i.e. FFPE and non-FFPE) for using sections of the cell block as a positive control for tissue based biomarker studies. The FFPE cell section has a defined number of cells with defined ratio. Said cell blocks are used as a standard for sensitivity and specificity evaluation in histological assay, but they are not used for calibrating fluorescence signals for quantification target molecules in a tissue sample.

European patent EP 1774292 E1 describes a calibration slide for fluorescence detection instruments and a process of preparing the same.

US 2004/0060987 A1 describes a method for detecting analytes using arrays of binding moieties. The arrays are attached to glass slides. Fluorescent signals obtained from the slides are analyzed by a digital image subtraction method. The glass slides can comprise calibration spots with known amounts of a FluoSphere.

SUMMARY

It is an objective of the present invention to provide for an improved image analysis method and image analysis system for determining the density of target molecules in a tissue sample depicted in a fluorescence image as specified in the independent claims. Embodiments of the invention are given in the dependent claims. Embodiments of the present invention can be freely combined with each other if they are not mutually exclusive.

In one aspect, the invention relates to an image analysis method for determining the density of target molecules in a tissue sample depicted in a fluorescence image. The method comprises:

receiving, by an image analysis system, a digital image of a slide; the slide comprises the tissue sample, a target dot and a fluoro dot; the fluoro dot comprises a known density of fluorescence-inducing molecules; the target dot comprises a known density of target molecules; the tissue sample and the target dot have been stained in the same staining procedure with the same type of fluorescence-inducing molecules as contained in the fluoro dot; the digital image comprises intensity values of the tissue sample, intensity values of the target dot and intensity values of the fluoro dot; the fluorescence-inducing molecules are adapted to directly or indirectly bind to the target molecules during the staining procedure;

receiving, by the image analysis system:
  pixel intensities of the fluoro dot depicted in the image;
  pixel intensities of the target dot depicted in the image;
  pixel intensities of an area of the tissue sample depicted in the image;
  fluorescence-inducing molecule density information indicative of the known density of the fluorescence-inducing molecules in the fluoro dot;
  target molecule density information indicative of the known density of the target molecules in the target dot;

computing, by the image analysis system, the density of target molecules in the area of the tissue sample as a function of the pixel intensities of the fluoro dot, the target dot, the area of the tissue sample, the fluorescence-inducing molecule density information and the target molecule density information.

Embodiments of the invention may have the advantage that—by using a new form of slide that comprises a fluoro dot and a target dot as described above and by using density information of the fluorescence-inducing molecules or target molecules in the respective dots—it is now possible to calibrate the intensity information of a fluorescence image in a way that the absolute number of target molecules in a tissue sample depicted in a fluorescence image can accurately and exactly be determined fully automatically by means of an image analysis method.

In one aspect, the method allows to normalize acquired intensity information by abstracting away the impact of optical components of the image acquisition system, e.g. the loss of intensity that occurs when fluorescence light traverses lenses and other components of a microscope and which may result in an underestimation of the number of target molecules.

In a further beneficial aspect, the method allows to normalize acquired intensity information by abstracting away the impact of a bad quality of the light source that stimulates the fluorophore to emit fluorescent light. For example, in case the light source of a first microscope is stronger than the light source of a second microscope, the fluorescence signal obtained by the first microscope for a particular slide and a particular tissue sample will be stronger than the fluorescence signal obtained by the second microscope for the same slide. However, as these factors affect the fluorescence-inducing molecules in the fluoro dot in the same way as the fluorescence-inducing molecules in the tissue sample, this effect can be computationally eliminated.

In a further beneficial aspect, the method allows to computationally eliminate the impact of parameters of the staining protocol on the fluorescence intensity. For example, fluorescence microscopy may be used for determining whether a particular cancer patient benefits from a particular treatment scheme. To test the efficiency of the anti-cancer drug, one or more tumor markers of a first biopsy sample of the patient may be labeled with a fluorescent stain before treatment for generating a first fluorescence image. Then, after some weeks of treatment, the same one or more tumor markers of a second biopsy sample of the patient may be labeled with the same fluorescent stain and are used for generating a second fluorescence image. As the number of fluorophore molecules that bind to a particular tumor marker (i.e., a form of target protein) may depend on the temperature and duration of the staining step, on the chemical composition of the staining buffer and other factors, it is currently not possible to accurately quantify the effect of a particular anti-cancer drug on the expression level of a tumor marker, because other factors (related to the sample handling and preparation procedures, the staining protocol, the hardware of the microscope, etc.) have also a significant impact on the intensity of a fluorescence signal.

However, by using two "calibration dots", i.e., the target dot and the fluoro dot, and the respectively known molecule densities, it may be possible to computationally eliminate the effect of said error sources on the fluorescence intensity, and to computationally determine the "real" number of target molecules contained in a particular tissue sample on the slide that comprises also the target dot and the fluoro dot. That the two calibration dots and the actually analyzed tissue sample are contained on the same slide may have the benefit that the molecules in the two dots and in the sample were subjected to the same staining procedure and that the pixel intensities received for the tissue sample region of the slide were received by the same image acquisition hardware as the pixel intensities of the calibration dots.

Embodiments of the invention combine knowledge derived from different domains such as image processing, microscopy, in particular fluorescence imaging, and wet lab procedures for enabling a more accurate assessment of the amount of target molecules contained in a sample.

According to embodiments, the computation of the density of the target molecules in the tissue area comprises:

computing the average intensity $I_{FID\_AVG}$ of the pixel intensities of the fluoro dot according to $$I_{FID\_AVG} = \frac{\sum I_{px\_FD}}{\#\text{pixel in } FD}$$

computing the average intensity $I_{TaD\_AVG}$ of the pixel intensities of the target dot according to:

$$I_{TaD\_AVG} = \frac{\sum I_{px\_TaD}}{\#\text{pixel in } TaD}$$

computing the ratio R of fluorescence-inducing molecules per target molecule in the target dot according to:

$$R = \frac{I_{TaD\_AVG}}{I_{FID\_AVG}};$$

computing the density δTarget_In_Tissue of the target molecules in the area of the tissue sample according to:

$$\delta_{Target\_In\_Tissue} = \frac{\frac{I_{TaD\_AVG}}{\mu m 2 \text{ tissue area}}}{\frac{I_{FID\_AVG}}{\mu m \ 2 \text{ target dot}}} \times \delta_{Target\_In\_Target\_dot} \times R,$$

wherein δTarget_In_Target_dot is the density of target molecules in the target dot.

For example, the average intensities $I_{FID\_AVG}$ and/or $I_{TaD\_AVG}$ can be computed as the arithmetic mean or as the median of the pixel intensity values received for the respective dots.

According to embodiments, the method further comprises coating an area of the slide with the target molecules, thereby creating the target dot.

For example, the coating can be performed by coating an area of the slide with a predefined number of the target molecules, thereby creating the target dot. The predefined number is then stored. For example, coating procedure may be performed such that it is ensured that a defined number of molecules per mm² are attached to the slide. The known molecule density can be printed or written onto the slide and/or can be stored in digital form in a database in association with an identifier of the slide or in association with an identifier of a set of slides coated in the same coating procedure or according to the same coating protocol. The molecule that is written or printed onto the slide may also be entered by a user, e.g. a lab worker, into the database. By using a coating technique with a known resulting molecule density, also the density of the target molecules in the target dot is "known", i.e., is available to the image analysis system, e.g. in the form of a data value stored in a digital storage medium.

Alternatively, the coating can be performed by coating an area of the slide with an unknown number of the target molecules, thereby creating the target dot, and then measuring the density of the target molecules in the target dot. For example, a particular single coating procedure may be performed for a large number of slides, e.g. several 100 or several 1000 or even several 10.000 slides. Then, the target molecule density in the target dot of one of sad slides or a small sub-set of said slides is empirically analyzed, e.g. by means of mass spectrometry, for determining the actual target molecule density in said few analyzed slides. In case the target molecule is a particular DNA or RNA sequence, the target molecule density in the target dot can be determined by means of quantitative PCR. The obtained target molecule density is then printed or written onto the slide and/or is stored in digital form in a database in association with an identifier of the slide or in association with an identifier of all slides coated in said single coating procedure as described already for the alternative coating approach.

According to embodiments, the coating of the area of the slide that shall constitute the target dot is performed using protein microarray technology.

According to embodiments, the method further comprises generating the target dot. The generation of the target dot comprises attaching reference cells homogenously to an area of the slide, thereby generating the target dot. The reference cells express or comprise a known number of the target molecules.

For example, the number of the target molecules in the reference cells can be determined empirically e.g. by mass spectrometry, cell cytometry, quantitative PCR (in case the target molecule is a DNA or RNA sequence of interest), etc. For example, a known number of reference cells may be attached to the slide an unknown number of the reference cells can be attached to the slide area that is to form the target dot and the density of the reference cells having been successfully attached to the slide is determined later after the target dot was created.

According to embodiments, the method further comprises, before the reference cells are attached to the slide: experimentally determining the average number of the target molecules which are expressed in or are contained in a set of reference cells (known to comprise the target molecule); and counting the number of cells attached to the target dot.

Said method may be beneficial, as it may not be necessary to extract and purify a particular target molecule, typically a biomarker, e.g. a particular protein or a particular RNA or DNA sequence, before it is used for coating the target dot with target molecules. Rather, it is possible to directly coat the target dot with reference cells known to comprise (e.g. express) the target molecules.

The reference cells can be attached to the slide by a coating technique or by generating homogeneous reference cell blocks as described e.g. in U.S. Pat. No. 9,395,283 and attaching the reference cell blocks as the target dots to the slides.

According to embodiments, the experimental determination comprises processing a reference tissue sample for transforming the reference tissue sample into a homogeneous suspension of reference cells; and experimentally determining the average number of target molecules comprised in the reference cells in the suspension or in a sub-set of the reference cells in the suspension. In addition, the number of cells per $mm^2$ of the target dot is determined empirically. The target molecule density in the target dot is then computed as a function of the empirically determined reference cell density in the target dot and the empirically determined average number of target molecules contained in each reference cell.

Said approach may be beneficial, because some target proteins cannot be extracted and purified from cells, or the extraction is highly complex. By coating an area of the slide with reference cells known to comprise the target molecules, basically any type of molecule that is comprised in at least one known type of cells can be used for generating the target dot. Further, the generation of the target dot by coating an area of the slide with reference cells comprising the target dot may more closely represent the environment provided by the tissue sample of the slide for the interaction of the fluorescence-inducing molecules with the target molecules.

According to embodiments, the experimental determination comprises performing a mass spectroscopy analysis or a flow cytometry analysis for quantitatively determining the number of target molecules in the reference cells. This may be beneficial, as said procedures are well established techniques for quantifying a particular molecule type in a cell or in any other material context. Although both methods tend to be complex, a growing number of semi-automated or automated systems exist which allow an accurate quantification of e.g. a particular protein in a particular cell or set of cells. It should be considered that this approach needs to be done only once for a representative sub-set of reference cells, and the same cell suspension may be used to create a large number of tissue slides with a respective target dot. Thus, performing the quantitative analysis for the reference cells to be used as the cells of the target dot once allows determining the "real" number of target molecules in a large number of tissue samples without respectively performing mass spectroscopy or flow cytometry analysis for each of said tissue samples individually. Thus, an accurate method of quantifying a target molecule in a tissue sample may be provided that does not necessarily require a complex analytical procedure such as mass spectroscopy or flow cytometry for each individual tissue sample.

According to embodiments, the ratio of fluorescence-inducing molecules that bind to a single target molecule during the staining procedure is unknown and depends on one or more parameters of the staining protocol. For example, the duration, temperature or solvent used during the staining process or while preparing a tissue sample for the staining protocol may have an impact on this ratio and may be an obstacle in determining the target molecule density based on the fluorescence signal intensity.

According to embodiments, the staining protocol is a tyramide signal amplification staining protocol ("TSA assay").

The sensitivity of immunohistochemical (IHC) fluorescence labeling depends on the properties of the fluorophore used for detection and on the amount of fluorophore present at the sites of antibody binding. Tyramide signal amplification (TSA, TSA assay) is a comparatively new enzymatic amplification procedure that deposits additional fluorophore molecules at the sites of antibody binding, thereby lowering IHC antigen detection limits. TSA can be utilized in single or multilabel IHC applications and can be coupled with quantum dots.

Traditional enzymatic IHC detection methods have utilized the ability of horseradish peroxidase (HRP) or alkaline phosphatase (AP) to convert a chromogenic substrate into a colored reaction product that precipitates at the site of enzymatic activity (Roth and Baskin, 2005; Roth and Perry, 2005). The sensitivity of HRP or AP detection can be improved upon by using "layering" techniques such as peroxidase-anti-peroxidase (PAP) or avidin-biotin complexes (ABC) that increase the number of enzyme molecules associated with the primary antibody. However, several factors limit the sensitivity and utility of these traditional enzymatic amplification procedures. In particular, multilabeling options and sensitivity may be limited.

To the contrary, TSA assays (respective kits are available e.g. from Perkin-Elmer, Waltham, Mass.) are much more sensitive and also support multilabeling. TSA is based on the ability of HRP, in the presence of low concentrations of $H_2O_2$, to convert labeled tyramide-containing substrate into an oxidized, highly reactive free radical that can covalently bind to tyrosine residues at or near the HRP (Bobrow et al., 1992; Adams, 1992; Shindler and Roth, 1996). Tyramide is prelabeled with a fluorophore, which is directly visualizable upon its deposition, or a hapten, which is then detected in subsequent steps with a hapten-specific reagent linked to a fluorophore or an enzyme molecule that can be used to deposit chromogen. In contrast to conventional fluorescence IHC detection methods (which utilize secondary antibodies labeled with a fluorophore), TSA results in the deposition of many more fluorescent molecules than can be linked to secondary antibodies. However, a downside of this amplification is that the degree of amplification depends on many parameters, e.g. parameters of the TSA Assay like temperature, staining duration, etc. and thus the strength of the fluorescence signal of a given number of target molecules may vary greatly in different TSA assays.

Embodiments of the invention may be particularly useful in the context of TSA assays, because the signal amplification and multi-labeling capabilities of the TSA assays can be used without reducing the accuracy of target molecule density determination, because the effect of the TSA assay parameters on the fluorescence signal intensity can be computationally eliminated by taking into account also the fluorescence intensities of the two calibration dots and the known molecule densities in the two dots.

According to embodiments, the binding of a fluorescence-inducing molecule to a single target molecule can be one of the following options:
  a covalent or ionic binding to the target molecule or to one or more intermediary molecules connected with the target molecule; for example, various covalently as well as non-covalently bound molecules (primary and/or secondary antibodies, avidine, biotine, and others) may be used to induce a fluorescence signal selectively in the vicinity of a target molecule;
  dipole-dipole interactions, Van-der-Waals interactions or hydrogen binding to the target molecule or one or more intermediary molecules connected with the target molecule;
  an antigen-antibody binding; for example, the fluorescent-inducing molecule can covalently bind to a primary antibody and the primary antibody can selectively bind to the target protein; according to another example, the fluorescent-inducing molecule can covalently bind to a secondary antibody, the secondary antibody can covalently bind to a primary antibody and the primary antibody can selectively bind to the target protein; in fact, in case the target dot already comprises molecule complexes of biomarker molecules and one or more primary antibodies bound to said biomarker molecule, and in case the number of said molecule complexes per mm2 target dot as well as the ratio of biomarker protein to primary antibody (or any other intermediary molecule) is known, the whole molecule complex constitutes a target molecule within the meaning of embodiments of the invention.
  a hybridization of nucleic acid sequences.

According to embodiments, the fluorescence-inducing molecules are fluorophores (e.g. an antibody labeled with a fluorophore).

According to alternative embodiments, the fluorescence inducing molecules are enzymes that trigger the emission of fluorescence signals by other molecules in spatial proximity to the fluorescence-inducing molecules (e.g. the horse radish peroxidase—HRP—enzyme: alone, the HRP enzyme, or conjugates thereof, is invisible; its presence must be made visible using a substrate that, when oxidized by HRP using hydrogen peroxide as the oxidizing agent, yields fluorescent signal).

Said features may be advantageous, as a plurality of commercially available kits exist for labeling different biomarkers with different fluorescent dyes. For example, the use of primary-secondary antibody labeling systems allows to use well established staining protocols for a particular fluorescent dyes for a large variety of different biomarkers simply by using different primary antibodies which all act as specific binding partner of a secondary antibody coupled to a fluorophore.

According to embodiments, the fluoro dot comprises a known density of further fluorescence-inducing molecules of at least one further type of fluorescence-inducing molecules. The tissue sample and the target dot both have been stained in addition with the further fluorescence-inducing molecules. The method comprises:
  receiving a further digital image of the slide, the further digital image comprising intensity values of the tissue sample, intensity values of the target dot and intensity values of the fluoro dot, the intensity values of the fluoro dot, the target dot and the tissue sample correlating with the number of the further fluorescence-inducing molecules in the fluoro dot, the target dot and the tissue dot, the further fluorescence-inducing molecules being adapted to directly or indirectly bind to the target molecules during the staining procedure;
  receiving:
    further pixel intensities of the fluoro dot depicted in the further image;
    further pixel intensities of the target dot depicted in the further image;
    further pixel intensities of the area of the tissue sample depicted in the further image;
    further fluorescence-inducing molecule density information indicative of the known density of the further fluorescence-inducing molecules in the fluoro dot;
  computing a further density of target molecules in the area of the tissue sample as a function of the further pixel intensities of the fluoro dot, the target dot, the area of the tissue sample, the further density information of the further fluorescence-inducing molecules and the target molecule density information.

For example, the receiving of the intensity information may be implemented as follows: the light source may emit light of a different excitation wavelength that selectively induces a fluorescence signal of the further fluorescence-inducing molecule, not of the first fluorescence-inducing molecule. Thereby, two different digital images are obtained which are analyzed as before for determining the respective target molecule densities from the one of the digital images whose pixel intensities are generated by florescence signals emitted by a respective one of the first or further fluorescence-inducing molecule.

Alternatively, a multispectral light source may be used, but different fluorescence filters may be used; for example, a first fluorescence filter may be used by the image acquisition system to receive a first digital image that selectively comprises fluorescence signals of the first fluorescence-inducing molecules (of the whole slide having been subjected to a staining procedure using the first fluorescent-inducing molecule, the first image including fluorescence signals of the fluoro dot, the target dot and of the tissue sample emitted by the first fluorescence-inducing molecules); a second fluorescence filter may be used by the image acquisition system to receive a second digital image that selectively comprises fluorescence signals of the further ("second") fluorescence-inducing molecules (of the whole slide having been subjected to the same or a different staining procedure using (also) the second fluorescence-inducing molecules, the second digital image including fluorescence signals of the fluoro dot, the target dot and of the tissue sample emitted by the further fluorescence-inducing molecules).

Depending on the staining protocols and the primary antibodies used, the two images may be used for quantifying the same type of target molecule twice (e.g. for obtaining a more accurate estimation of the target molecule density which is based on the use of two independent staining approaches with two different fluorescent labels, or for quantifying multiple different target molecules in the same tissue concurrently.

Like the density information of the first fluorescence-inducing molecules, the further fluorescence-inducing molecule density information indicative of the known density of the further fluorescence-inducing molecules in the fluoro dot can be received by the image analysis system e.g. by reading respective data values from a storage medium, e.g. a non-volatile storage medium.

Thus, multiple biomarkers may be stained with different fluorophores often within the same staining protocol.

Said features may be advantageous, because a slide whose fluoro dot comprises two or more types of fluorescence-inducing molecules may allow the accurate determination of the densities of multiple different target molecule types provided said different target molecule types are labeled with a fluorescence-inducing molecule that is comprised in the fluoro dot.

Alternatively, the same type of target molecules in the target dot and in the tissue sample of the slide may be stained with different fluorescence-inducing molecules.

According to embodiments, the method further comprises computing the average of:
the density of the target molecules in the area of the tissue sample computed according to any one of the embodiments described herein, and
the further density of the target molecules in the area of the tissue sample computed according to any one of the embodiments described herein.

Thus, by performing the intensity calibration with the two calibration dots for each of the two or more fluorescent-inducing molecule types separately, and then e.g. computing an average target molecule density value, an even more accurate determination of the number of target molecules in a particular tissue sample may be achieved.

According to embodiments, the target molecule is selected from a group comprising:
a biomarker molecule;
a primary antibody capable of selectively binding to the biomarker molecule in a predefined molecular ratio;
a secondary antibody capable of selectively binding to the primary antibody in a predefined molecular ratio.

In a further aspect, the invention relates to an image analysis system configured for determining the density of target molecules in a tissue sample depicted in a fluorescence image. The system comprises a storage medium and one or more processors configured for:
receiving a digital image of a slide, the slide comprising the tissue sample, a target dot and a fluoro dot, the fluoro dot comprising a known density of fluorescence-inducing molecules, the target dot comprising a known density of target molecules, the tissue sample and the target dot having been stained in the same staining procedure with the same type of fluorescence-inducing molecules as contained in the fluoro dot, the digital image comprising intensity values of the tissue sample, intensity values of the target dot and intensity values (120) of the fluoro dot, the fluorescence-inducing molecules being adapted to directly or indirectly bind to the target molecules during the staining procedure;
receiving:
pixel intensities of the fluoro dot depicted in the image;
pixel intensities of the target dot depicted in the image;
pixel intensities of an area of the tissue sample depicted in the image;
fluorescence-inducing molecule density information indicative of the known density of the fluorescence-inducing molecules in the fluoro dot;
target molecule density information indicative of the known density of the target molecules in the target dot;
computing the density of target molecules in the area (154) of the tissue sample as a function of the pixel intensities of the fluoro dot, the target dot, the area of the tissue sample, the fluorescence-inducing molecule density information and the target molecule density information.

In a further aspect, the invention relates to a slide comprising a tissue sample, a target dot and a fluoro dot, the fluoro dot comprising a known density of fluorescence-inducing molecules, the target dot comprising a known density of target molecules.

According to embodiments, the slide with the tissue sample and the target dot has been stained in the same staining procedure with the same type of fluorescence-inducing molecule as contained in the fluoro dot. The fluorescence-inducing molecules is adapted to directly or indirectly bind to the target molecules (known to be contained in the target dot and suspected of being contained in the cells of the tissue sample) during the staining procedure.

According to embodiments, the fluoro dot of the slide comprises a known density of further fluorescence-inducing molecules of at least one further type of fluorescence-inducing molecules. The further fluorescence-inducing molecules are adapted to directly or indirectly bind to the target molecules during the staining procedure.

This type of slides may be used for computing the target molecule density in the tissue sample as an average of the target molecule densities obtained individually for the different fluorescence-inducing molecules. "Different" fluorescence inducing molecules as used herein are fluorescence-inducing molecules having a distinguishable fluorescence emission spectrum.

According to other embodiments, the fluoro dot of the slide comprises a known density of further fluorescence-inducing molecules of at least one further type of fluorescence-inducing molecules. The further fluorescence-inducing molecules are adapted to directly or indirectly bind to further target molecules of a further target molecule type during the staining procedure. The target dot in addition comprises a known density of the further target molecules. For example, the first and the further ("second") target molecules can be two different biomarkers.

According to embodiments, the target dot is an area of the slide that is coated with a known number of the target molecules or that is coated with a known number of cells, the cells expressing or comprising a known number of the target molecules.

An "image analysis system" as used herein is an electronic system, e.g. a computer, configured for extracting meaningful information from digital images by means of digital image processing techniques. Image analysis tasks can comprise color deconvolution, connected component analysis, image segmentation and/or edge detection for identifying dots, tissue samples, individual cells, the type of the cells (tumor or stroma cell, different types of immune cells) and the like. In some embodiments, an image analysis system can further comprise or be operatively coupled to an image acquisition system, e.g. a microscope.

A "target molecule" as used herein is a molecule, molecule part (e.g. a gene sequence contained in genomic DNA), or molecule complex (e.g. an epitope bound to one or more intermediary molecules, the intermediary molecule(s) being the actual binding partner(s) for a fluorescence-inducing molecule) whose quantity in a tissue sample shall be determined. For example, the target molecule can be a biomarker, or biological marker, i.e., an indicator of some biological state or condition. Biomarkers are often measured and evaluated to examine normal biological processes, pathogenic processes, or pharmacologic responses to a therapeutic intervention. A known density of the target molecule is attached to a region of the slide which is referred herein as "target dot". A target molecule as used herein can also be a specific sub-sequence of a nucleic acid molecule that is of particular interest, e.g. a gene sequence in a DNA molecule.

A "fluorescence-inducing molecule" as used herein is a molecule that is itself capable of emitting fluorescent light in response to absorbing light or other electromagnetic radiation (a "fluorophore", e.g. an antibody coupled to fluorescein) or is a molecule that is capable of inducing fluorescence in specific other molecules in its spatial neighborhood (e.g. a HRP complex). In most cases, the emitted light has a longer wavelength, and therefore lower energy, than the absorbed radiation. Many fluorescent stains have been designed for a range of biological molecules. Some of these are small molecules which are intrinsically fluorescent and bind a biological molecule of interest. Major examples of these are nucleic acid stains like DAPI and Hoechst (excited by UV wavelength light) and DRAQ5 and DRAQ7 (optimally excited by red light) which all bind the minor groove of DNA, thus labeling the nuclei of cells. Others are drugs or toxins which bind specific cellular structures and have been derivatised with a fluorescent reporter. A major example of this class of fluorescent stain is phalloidin which is used to stain actin fibres in mammalian cells. There are many fluorescent molecules called fluorophores or fluorochromes such as fluorescein, Alexa Fluors or DyLight 488, which can be chemically linked to a different molecule which directly or indirectly binds to a target molecule of interest within the sample and within the target dot.

A "fluorescence microscope" as used herein is an optical microscope that uses fluorescence and phosphorescence instead of, or in addition to, reflection and absorption to study properties of organic or inorganic substances. A "fluorescence microscope" refers to any microscope that uses fluorescence to generate an image, also referred to as "digital fluorescent image", whether it is a more simple set up like an epifluorescence microscope, or a more complicated design such as a confocal microscope, which uses optical sectioning to get better resolution of the fluorescent image.

A "tissue sample" as used herein is matter having been gathered from the body of an organism, e.g. a mammal, e.g. a human. The tissue sample can be, for example, a tumor tissue sample, a blood smear sample, a skin tissue sample, or the like. Tissue samples can be stained with fluorescent or other stains and can be attached to microscope slides for enabling an image acquisition system to generate digital images of the sample that can be analyzed. The image analysis can be performed e.g. to aid in the process of a medical diagnosis and/or evaluation of an indication for treatment, further medical tests or other procedures.

A "fluorescence image" as used herein is a digital image whose pixels have pixel intensities which are indicative of fluorescence signals captured by a fluorescence microscope or by another fluorescence-based image acquisition system.

A "dot" as used herein is an area of a slide. The dot may have any shape, e.g. a rectangular, square or circular shape.

The "density" of a molecule in a dot as used herein is the number of molecules in a given area unit, e.g. $mm^2$. A "known" molecule density means that the density of the respective molecule type was already known when an image analysis method for quantifying target molecules in a tissue sample is carried out. For example, the molecule density can have been determined empirically in advance before or while a particular calibration dot was created on the slide.

A "slide" as used herein is a carrier structure for tissue samples that is used for generating digital images of the tissue sample, in particular fluorescence images. Preferentially, the slide is a microscope slide. The slice can be e.g. a glass slide that can be coated with one or more layers that facilitate or enable the adhesion of target molecules, fluorescence-inducing molecules and/or reference cells to the slide.

A "tyramide signal amplification staining protocol", also called "TSA assay" or "CARD" for Catalyzed Reporter Deposition, is an enzyme-mediated detection method that utilizes the catalytic activity of an enzyme (typically horseradish peroxidase—HRP) to generate high-density labeling of a target protein or nucleic acid sequence in situ. TSA has been reported to increase detection sensitivity up to 100-fold, as compared with conventional avidin-biotinylated enzyme complex (ABC) procedures. Moreover, for multiparameter detection of targets in either live or fixed cells or tissues, TSA can be combined with several other important technologies, including our nucleic acid labeling kits, primary and secondary antibodies, avidin and lectin conjugates, cytoskeletal stains, and others. According to preferred embodiments, TSA labeling is a combination of at least three elementary processes that typically comprise: a) binding of a probe to the target via immunoaffinity (proteins) or hybridization (nucleic acids) followed by secondary detection of the probe with an HRP-labeled antibody or streptavidin conjugate. Peroxidase conjugates of other targeting proteins such as lectins and receptor ligands are likely to be suitable for labeling targets, as is endogenous peroxidase activity; b) activation of multiple copies of a labeled tyramide derivative by HRP; often, a fluorescent or biotinylated tyramide is used; c) covalent coupling of the resulting highly reactive, short-lived tyramide radicals to residues (principally the phenol moiety of protein tyrosine residues) in the vicinity of the HRP-target interaction site, resulting in minimal diffusion-related loss of signal localization. Using a slide with a fluoro dot and a target dot in the context of a TSA assay may be particularly advantageous because the increased signal strength of the TSA assay is typically accompanied by a high variability of the signal amplification strength and thus with a large uncertainty regarding the actual amount of target contained in a tissue sample. Using a slide with a fluoro dot and a target dot in the context of a TSA assay may allow benefitting from the high sensitivity of the TSA protocol and at the same time being able to estimate the amount of target molecules in the sample.

BRIEF DESCRIPTION OF THE DRAWINGS

In the following embodiments of the invention are explained in greater detail, by way of example only, making reference to the drawings in which.

DETAILED DESCRIPTION

Figure 1:
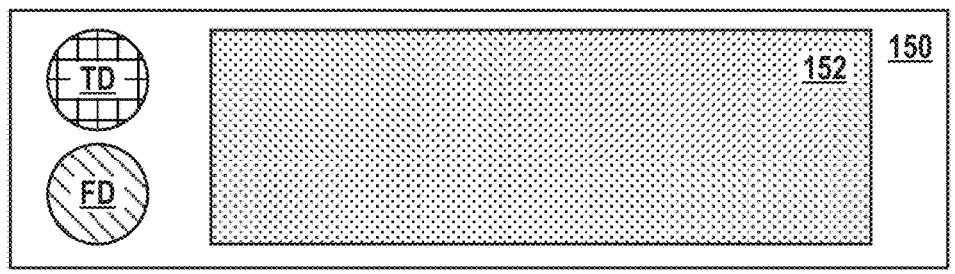
FIG. 1 is a block diagram of a tissue slide.

FIG. 1 shows a slide 150 that comprises a fluoro dot FD, a target dot TD and a tissue sample. The slide can be, for example, a glass tissue slide. In a first area FD referred herein as "fluoro dot", the slide is covered by fluorescence-inducing molecules of a known molecule density. In a second area TD referred herein as "target dot", the slide is covered by target molecules of a known molecule density. In a third area of the slide, the slide comprises a tissue sample 152, e.g. of a mammal, e.g. a tissue sample of tumor tissue of a patient.

Typically, the slide is used for examining the location of a particular type of molecule of interest, referred herein as "target molecule" and for determining the density (e.g. the "expression level" in case the target molecule is a protein) of the target molecules in the tissue sample. For example, the target molecules can be a biomarker for a particular tumor-subtype, e.g. Her2, BRCA1, BRCA2 or the like.

The target dot TD comprises a known density of the target molecule. Several different methods can be used for generating a target dot having a known target molecule density. For example, the slides can be coated with a defined number of isolated target molecules or with a defined number of reference cells whose target molecule concentration is known. For example, the target molecule concentration and the reference cells can be determined by homogenization of a reference tissue known to comprise the target molecules, generating a suspension of the reference cells, empirically determining the amount of target protein in the reference cells, e.g. by mass spectrometry or by fluorescence cytometry or other appropriate technical means. Then, either a defined number of reference cells is attached to the surface of the slide 150, or the suspension of reference cells is used for attaching an unknown number of reference cells on the surface of the slide and later counting the number of reference cells per mm2 which have been successfully attached to the surface of the slide. This counting can be performed manually or automatically by means of image analysis techniques which are able to automatically identify and count cells. The same homogeneous suspension of reference cells can be used for coating a plurality of slides, e.g. several hundred, several thousand or even more slides. As a homogeneous suspension of reference cells was used for coating the tissue slide, the determination of the reference cell density in the target dots of only a few slides may be sufficient for determining and "knowing" also the reference cell density of the target dots of all the other slides coated based on the same homogeneous reference cell suspension. As the average target molecule concentration in each reference cell was also determined empirically in the reference cells, it is possible to determine and compute the target molecule density in the target dot TD. This "known" target molecule density can optionally be printed onto the slide 150 and/or can be stored in a storage medium.

The fluoro dot FD comprises a known density of the fluorescence-inducing molecules molecule. Several different methods can be used for generating a fluoro dot having a known fluorescence-inducing molecule density. For example, the slides can be coated with a defined number of isolated fluorescence-inducing molecules. Alternatively, a large number of slides can be coated with the same homogeneous suspension (or solution) of fluorescence-inducing molecules. The density of the fluorescence-inducing molecules that actually become firmly attached to the slides to form the fluoro dots can later be empirically determined, e.g. by means of mass spectrometry or other appropriate analytical methods. Provided, the same suspension/solution of fluorescence-inducing molecules was used for coating the slides, it is sufficient to empirically determine the reciting fluorescence-inducing molecule density on only a few slides and respective fluoro dots. This "known" fluorescence-inducing molecule density can optionally be printed onto the slide 150 and/or can be stored in a storage medium.

Preferably, the fluoro dot actually comprises a mixture of two or more different types of fluorescence-inducing molecules, whereby the density of each of that different types of fluorescence-inducing molecules is known (the densities of said different types of molecules may or may not be identical). This may allow a user to flexibly choose a particular fluorescent dye for staining a target molecule of interest among a plurality of different fluorescent dyes which are commercially available. Thus, a user is not limited to a single a particular fluorescent dye or fluorescence-inducing molecule that was used for generating the fluoro dot. Moreover, a user of a slide comprising a fluoro dot with two or more different fluorescence-inducing molecule types can perform multi-color fluorescence image analysis and can stain and quantify multiple different types of target molecules in a single experimental procedure. For example, the user can use different fluorescence filters or can use a light source with a defined excitation spectrum to induce the emission of fluorescence signals selectively by a particular one of the fluorescence-inducing molecules in the fluoro dot (and the target dot and the tissue sample of the slide), thereby creating a fluorescent image that selectively indicates the presence of this particular fluorescence-inducing molecule (and any target protein to which it is selectively attached).

The whole slide with the target dot, the fluoro dot and the tissue sample is subjected to a staining procedure during which the same fluorescence-inducing molecule that is contained in the fluoro dot becomes selectively attached to the target molecules in the target start and to the target molecules in the tissue sample 152, if any. Although the actual number of fluorescence-inducing molecules which become attached to a single target molecule may be unknown, e.g. because that attachment ratio strongly depend on the particularities of the staining procedure, it can safely be assumed that the attachment ratio is the same for the target molecules in the target dot as for the target molecules in the tissue sample 152. As the target molecule density in the target dot and the fluorescence-inducing molecules in the fluoro dot are known and as the fluorescence signal intensities of the target starts, the fluoro dot and the tissue sample 152 have been captured by the same image acquisition system (e.g. the same fluorescence microscope), the target dot and the fluoro dot can be used for calibrating the intensity information obtained for the tissue sample and can be used for accurately determining the target molecule density in the tissue sample 152.

In order to generate the target dot of one or more slides as depicted in FIG. 1, a reference tissue is taken from a tissue known or suspected to comprise a particular target molecule.

For example, a tissue biopsy can be prepared as formalin-fixed paraffin-embedded (FFPE) sample. FFPE preps can be stored indefinitely at room temperature, allowing the nucleic acids (both DNA and RNA) to be recovered and analyzed even decades later.

In order to generate the target dot, a slice or punch from an FFPE reference sample is de-paraffinized and a suspension of reference cells stained for one or more types of target molecules (e.g. keratin, vimentin or a particular DNA/RNA sequence) is generated from the reference sample. Flow cytometry is then applied to all or a subset of the reference cell in the suspension to determine the number of target molecules in the reference cells. Optionally, the reference cells in the suspension can be sorted to remove cells which do not comprise the target protein or which do not comprise the target protein in a desired quantity range. For example, commercially available systems and methods such as the DEPArray system's image-based sorting can be used for selectively obtaining reference cells which express the target protein in a desired amount range. Thus, a highly pure collection of reference cells with known target molecule density can be recovered from FFPE tissue samples and can be used for coating a specific area of the tissue slide with the reference cells. The density of reference cells that actually become firmly attached to the target dot may be empirically known from previous coating procedures under the same coating conditions or may be determined for one or more of the generated target dots later by manually or automatically counting the cells. Thus, the target molecule density in the target dot is computed (and thus "known") from the empirically determined target molecule concentration in the reference cells and from the density of reference cells which become firmly attached to the slide, thereby forming the target dot. The creation of homogeneous cell blocks and the attachment of said cell blocks on slides, e.g. for the purpose of providing a positive control for biomarkers in immunohistochemistry experiments, is described for example in U.S. Pat. No. 9,395,283 B1 which is incorporated herewith by reference in its entirety.

For example, reference cells known to comprise a particular target molecule of interest are pre-treated and stained with a fluorescent dye or other fluorescence-inducing molecule. Then, the target molecule density in the cell block is empirically determined. The density of the reference cells within the final block is controlled by adjusting the size of a mold used for forming the cell blocks in order to produce a target dot comprising cells of a certain number/density/count of target molecules, wherein the target dot comprises a particular number of reference cells. The reference cell blocks have a defined size and length to control the number of reference cells in each block, thereby producing a target dot comprising a certain number (i.e. pre-designated, "known" number) of reference cells with a known density (or concentration) of respective target molecules.

The steps in the method of making the target dot (i.e. cell block) comprise: a) passing reference cells through a cell collection device, wherein said reference cells are in suspension, fixed pellet, or unfixed pellet form; b) performing reference cell counting; c) fixing the cells in a composition comprising paraformaldehyde in PBS to create a "cell pellet" or "cell block"; d) preparing the molds; re-suspending the cells in PBS; and immobilizing the suspension in controlled temperature; e) injecting the cell suspension into the prepared mold of predefined size and shape at a controlled temperature; f) cooling and treating the cells with a paraffin processor; and, g) performing molecule quantification, e.g. DNA extraction and quantification or mass spectrometry; the information obtained during this step may in addition be used to check and verify that the reference cells are distributed homogeneously in the cell block.

The cell block preparation step in the above described method of making the cell block comprises: a) passing reference cells through an apparatus to create a homogenous mixture of immobilized cells; b) injecting the homogeneous reference cell mixture into a Mold A ("first mold", e.g. a mold being 4 mm in radius, 145 mm in length), and remove the generated reference cell blocks from the mold; and, c) processing cell blocks with paraffin, removing individual blocks from paraffin, and embedding the processed cell blocks into a Mold B ("second mold", e.g. a cubed paraffin Mold of 2 cm *2 cm *2 cm). The cell blocks are wrapped with parafilm and kept in air-tight box at 4° C. until they are sectioned in multiple tissue block sections that are attached to the slide and are respectively used as target dots.

According to embodiments, reference cell blocks of a specific, known reference cell density are created by mixing the suspension of reference cells with agarose, e.g. 3% agarose, whereby the amount of agarose is chosen such that the resulting reference cell/agarose mixture that is to be filled into the second mould has the desired reference cell density.

Preferentially, the reference cells attached to the slide are homogeneously distributed in the target dot. The detection of homogeneity can be performed using cell counting, e.g. by digital immunohistochemistry devices (e.g. Aperio ScanoScope). Detection of homogeneity can also be confirmed by the extraction and quantification of nucleic acids from each cell block section to determine the amount of nucleic acids in each block and the ratio of a mixture of cells within the block. Methods of DNA extraction and quantification are, for example, PCR, digital PCR and/or sequencing methods.

Alternative methods of creating the target dot can be used as well: for example, in case the target molecule is a protein that is available or can be prepared in purified form, protein coating techniques as used for the production of protein microarrays can be used for firmly attaching the protein in a desired amount on the surface of the slide. Several techniques of attaching proteins to slide surfaces are disclosed e.g. in the paper "*Systematic comparison of surface coatings for protein microarrays*" of Birgit Guilleaume et al., Proteomics 2005, 5, 4705-4712 4705, WILEY-VCH Verlag GmbH & Co. KGaA, which is incorporated herewith by reference in its entirety. Further documents which describe a method of coating of modified glass slides with a particular protein which can be applied for generating the target are, for example:

Peluso, P., Wilson, D. S., Do, D., Tran, H. et al., Anal. Biochem. 2003, 312, 113-124.

Zhu, H., Klemic, J. F., Chang, S., Bertone, P. et al., Nature, Genet. 2000, 26, 283-289.

Mac Beath, G., Schreiber, S. L., Science 2000, 289, 1760-1763.

Stillman, B. A., Tonkinson, J. L., Biotechniques 2000, 29. 630-635.).

The above cited documents mainly involve covalent attachment of proteins via different functional groups that are coupled to the surface. The most commonly used functional groups are epoxy, aldehyde, and Nhydroxysuccinimide (NHS)-ester. In contrast, am inosilane coatings immobilize proteins via electrostatic forces.

According to some embodiments of the method, the method comprises generating the fluoro dot by coating an area of the slide with fluorescence-inducing molecules.

For example, US patent US2003/0015668, which is incorporated in this patent specification by reference in its entirety, discloses a method to deposit an extremely thin layer of Cy3, Cy5 or other fluorescent dye doped glass by evaporation or sol-gel process on a non-fluorescent support.

According to another example, the fluoro dot can be created by any one of the calibration dot creation methods descried in EP 1774292 B1 which is incorporated in this patent specification by reference in its entirety. Said document describes rare-earth ion doped inorganic arrays for calibration of fluorescence microarray scanners and a process of making them. Surfactants or dispersants are employed to help the coated inorganic phosphors disperse evenly in aqueous suspensions. Any suitable one or mixture of the surfactants, e.g., Tween-20, Triton-100, sodium lauryl sulfate (SLS), polyethylene glycol (PEG) 2000, PEG 4000, PEG 6000, PEG 8000, PEG 10000, PEG 20000, polyvinyl alcohol (PVA), polyethylene imine (PEI), sodium polyacrylate (PAA) can be used in the suspension of the inorganic phosphors. The quantity of said surfactants may be 0.1%~10%, more preferably 0.1-5%, Preferably, a spotting agent, e.g., dimethyl sulfoxide (DMSO) or glycerol is added in said suspension of inorganic phosphors. The slide may be prepared by the following methods: the fluoro dot is spotted on the slide by a contact printer or by spin coating and screen printing techniques. The diameter of the fluoro spots can e.g. be in a range of 100-500 μm, more preferably 120-300 μm, but it can also have any other size.

The fluoro dot and the target dot can be applied on a standard microscope glass slide having e.g. a dimension of 75.6 mm×25 mm×1 mm. The surface of the glass slide may be unmodified or modified. For example, the glass slide to carry the fluoro dot can be globally or locally modified by a chemical method, i.e. amino-modified slide, aldehyde-modified slide, epoxy-modified slide, thiol-modified slide or polymer film modified slide, i.e, PVA film, agarose film, or the mixing of PVA and agarose film. A very thin layer can be deposited on the slide surface to protect the fluoro dot comprising said inorganic phosphors, Thus, a transparent thin film of polydimethylsiloxane (PDMS) or PVA with low fluorescence background may be created, whereby the thickness of the film is preferably less than 50 μm. Further details of the method are described in EP 1774292 B1, In dependence on the fluorescence-inducing molecule used, the protocol may be adapted to the particular property of the respective fluorescence-inducing molecule.

Figure 2:
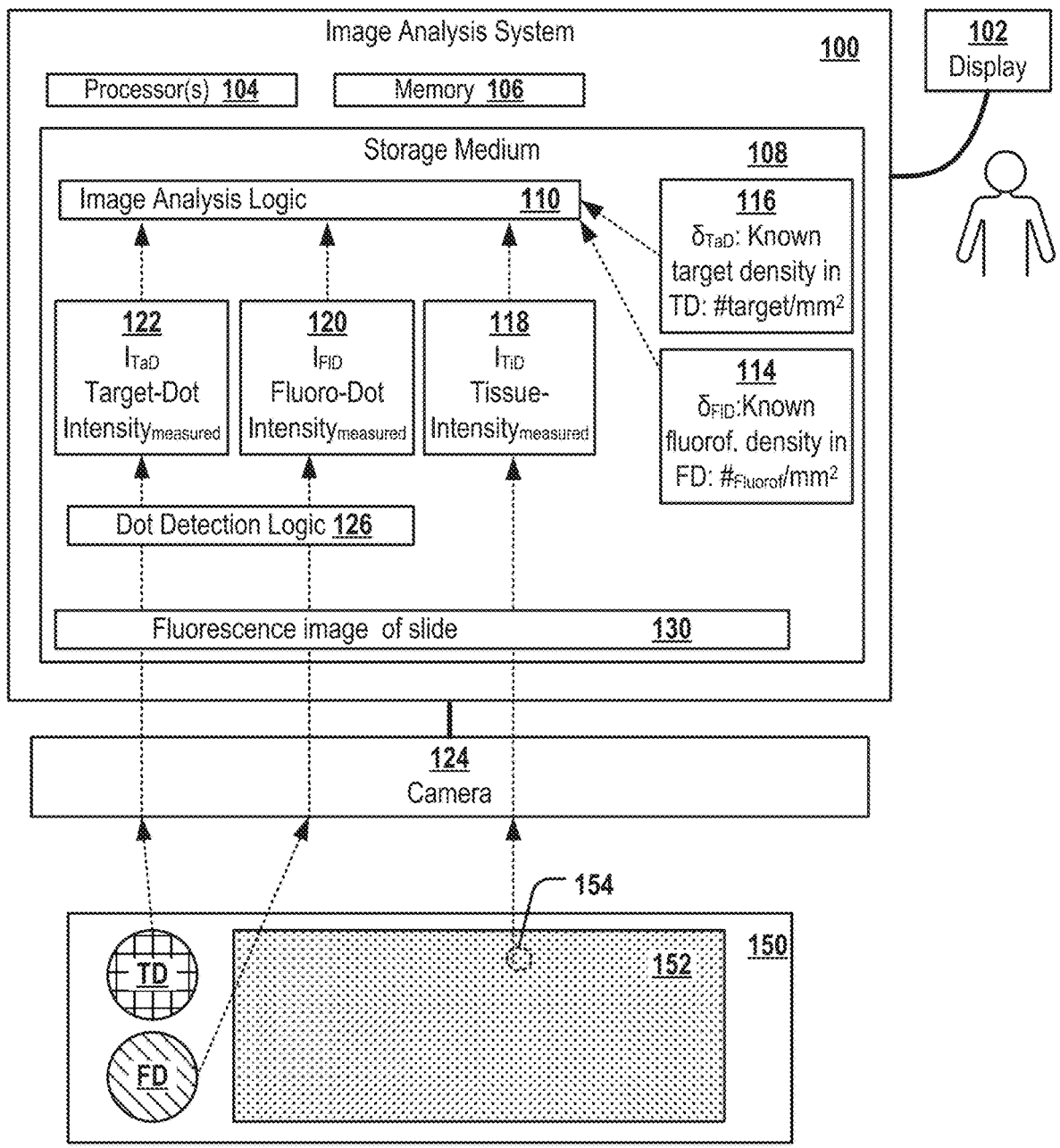
FIG. 2 is a block diagram of an image analysis system configured for analyzing a fluorescence image of a slide.
Figure 3:
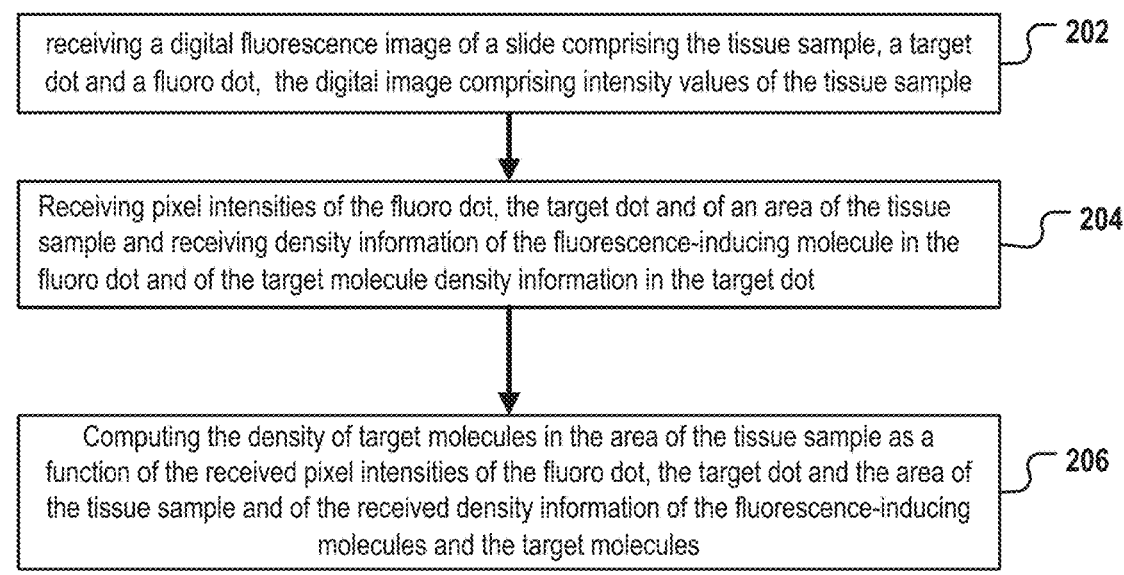
FIG. 3 is a flow chart of a fluorescence image analysis method for quantifying target molecules in a tissue sample.

FIG. 2 is a block diagram of an image analysis system 100 according to an embodiment of the invention. The system comprises one or more processors 104, a main memory 106 and a non-volatile storage medium 108. The storage medium comprises computer-interpretable instructions 110, 126 configured for performing an image analysis method for determining the density of the target molecules in a tissue sample 152 as described herein for embodiments of the invention and as depicted in the flowchart of FIG. 3. The system may optionally comprise or be coupled to an image acquisition system 124, e.g. a camera, for receiving a fluorescence image 130 of a slide 150 as depicted, for example, in FIG. 1. In addition, or alternatively, the fluorescence image 130 is stored on the storage medium 108. The storage medium 108 may comprise instructions for a dot detection log 126 which is configured for performing an image analysis of a whole slide image 130 of the fluorescence slide for automatically detecting the regions in the digital image 130 which corresponds to the fluoro dot, the target dot and the tissue sample 152. In addition, or alternatively, the coordinates of the two calibration dots can be pre-configured and stored in the storage medium and can be used for quickly and accurately identifying the pixels in the digital image which corresponds to the respective calibration dots.

Thus, in step 202 the image analysis system 100 may retrieve a digital fluorescence image 130 of the slide 150 directly via the corner out 124 or by reading an existing fluorescence image 130 from the storage medium 108.

Then in step 204, pixel intensities of different regions of the image which corresponds to the target dot, the fluoro dot or the tissue sample are received. For example, a dot detection logic 126 automatically identifies pixel regions corresponding to the fluoro dot, to the target starts and to the tissue sample. Then, the image analysis logic 110 can compute the average intensity 122 of the pixels corresponding to the target dot, the average intensity 120 of the pixels corresponding to the fluoro dot and the average intensity 118 of an area of interest 154 within the tissue sample. The area of interest 154 can be a single pixel (whose intensity value is used instead of the "average" intensity value) or can be a set of pixels whose combined analysis is still considered as sufficiently detailed to extract the biomedical information of interest. The number of pixels that constitutes the area of interest 154 may depend on the particular experimental setting and the medical question, but typically comprises fewer pixels than are contained in a pixel area typically corresponding to the size of a cell. Preferably, the fluorescence intensity values of all pixels corresponding to the tissue sample are analyzed and calibrated such that the real number of target molecules in the respective tissue sample region can be determined. Thus, the determination of target molecule density region 154 is described just as an example for demonstrating how the totality of tissue sample pixels can be analyzed according to embodiments of the invention. The obtained intensity information 122, 120 and 118 can optionally be stored in the storage medium 108.

Then, the image analysis logic 110 reads the known density information 116 indicating the target molecule density in the target dot TD and the known density information 114 indicating the fluorescence-inducing molecule density in the fluoro dot FD.

Then in step 206, the image analysis method 110 computes the target molecule density in the area 154 of interest as a function of the measured intensity values 1 to 2, 120 and 118 and the "known" molecule densities 114, 116 of the respective calibration dots TD, FD.

Figure 4:
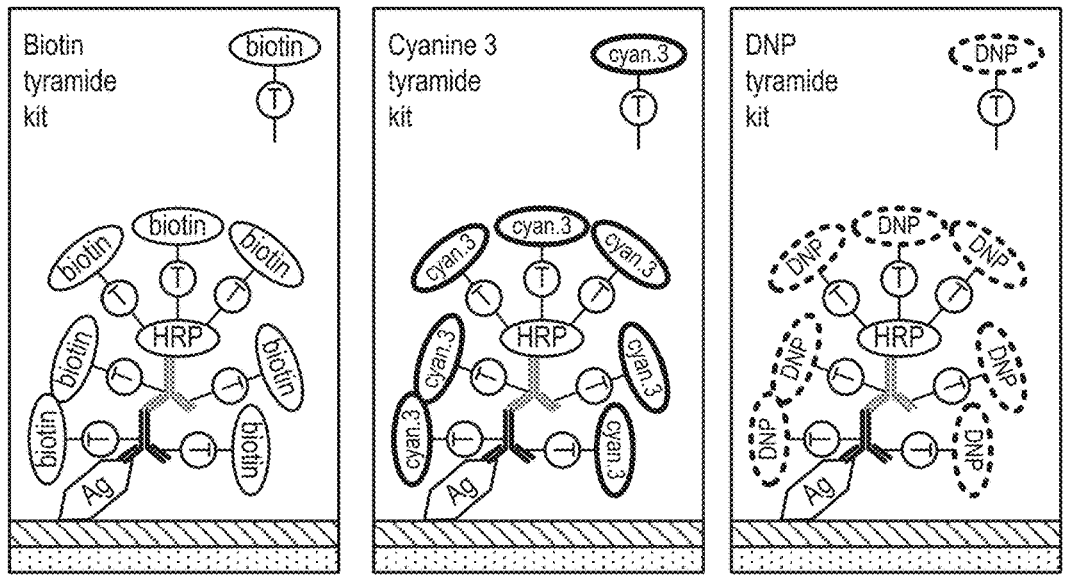
FIG. 4 depicts three different tyramide signal amplification assays.
Figure 4:
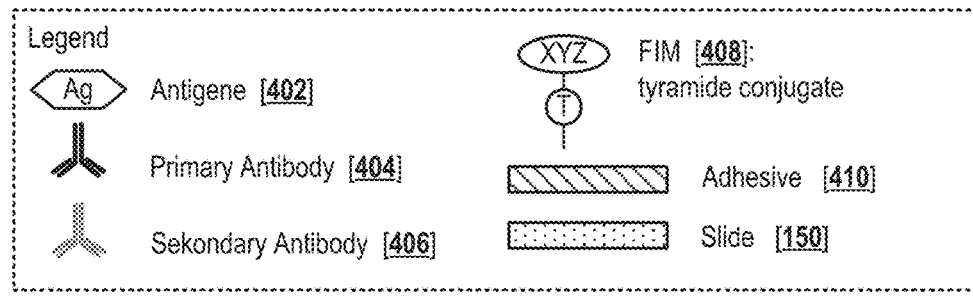

FIG. 4 depicts three different tyramide signal amplification assays for which respective kits are commercially available. Tyramide Signal Amplification (see e.g. U.S. Pat. Nos. 5,731,158, 5,583,001 and 5,196,306) amplifies fluorescent signals in many applications. TSA can be used for increasing sensitivity in any application that allows the addition of horseradish peroxidase (HRP) into its protocol, such as immunohistochemistry, in situ hybridization, ELISA and microarray-based differential gene and protein expression studies. HRP is used to catalyze the deposition and binding of a labeled (e.g., biotin, DNP or other labeling moieties) tyramide onto tissue sections or cell preparations comprising a target molecule, typically a biomarker, e.g. a protein such as CD20, CD4, CD45RO, CD68, FOXP3, panCK, and other custom targets. The binding is covalent because the reaction intermediately dimerizes with tyrosine residues on the surface-bound endogenous proteins. These labels can then be detected by standard fluorescent techniques. Since the added labels are only deposited proximal to the enzyme site, the fluorescence signal is selectively indicative of the presence and amount of a target molecule. If the fluoro dot comprises fluorescence-inducing molecules of two or more different types and if the slide 150 is labeled with two or more respective fluorescence-inducing molecules, multi-target detection in the same sample is of interest is supported. A further beneficial aspect of using TSA is that unamplified detection levels can be maintained while utilizing up to 1,000-fold less primary antibody.

The TSA amplification reagent is a phenolic compound that, when activated by HRP, is converted into a short-lived, extremely reactive free radical intermediate. This free radical intermediate reacts rapidly with and covalently binds to electron-rich regions of adjacent proteins (predominantly tyrosine residues). This binding occurs adjacently to the sites at which the HRP enzyme is bound. HRP catalyzes the deposition and covalent binding of the fluorophore- or hapten-labeled TSA substrate onto tissue sections comprising the target molecules. In FIG. 4, an antigen (Ag 402) may represent an epitope of a target molecule of interest. The target molecule may be attached e.g. via an adhesive layer 410 directly to the slide 150, e.g. in the target dot TD, or can be attached to the slide as an element a cell (e.g. a reference cell in the target dot or a tissue cell in the tissue sample). The black antibody 404 represents a primary antibody that selectively binds to the antigen. The grey antibody 406 is a secondary antibody that together with the HRP enzyme forms a secondary antibody/HRP conjugate. "T" is a tyramide with fluorescent label for visualization. The fluorophore-labeled TSA substrate can be, for example, a biotin-tyramide conjugate, cyanine-3-tyramide conjugate or a DNP (dinitrophenol)-tyramide conjugate.

By increasing the sensitivity 10-200 times that of standard ICC/IHC/ISH methods, applying a TSA assay on a slide comprising a target dot and a fluoro dot and applying the image analysis method as described herein for embodiments of the invention allows to accurately quantify even low-abundance targets.

Figure 5:
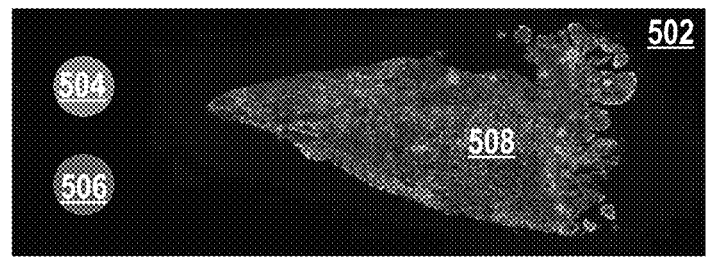
FIG. 5 is a fluorescence image of a slide according to embodiments of the invention.

FIG. 5 shows a fluorescence image 502 of a slide according to embodiments of the invention. Pixel region 504 corresponds to the target dot TD, pixel region 506 corresponds to the fluoro dot FD and tissue sample pixel region 508 corresponds to a tissue sample 152. For example, the pixel regions 504, 506 and 508 can be automatically identified by various image analysis techniques such as blob detection, image segmentation, and/or edge detection methods. By changing the fluorescence filter or the excitation light source and the respective excitation wavelength, a further fluorescence image can be generated whose intensities are indicative of a different target protein labeled with a different fluorescence-inducing molecule or whose intensities are indicative of the same target protein labeled with the different fluorescence-inducing molecule.

The invention claimed is:

1. An image analysis method for determining the density of target molecules in a tissue sample depicted in a fluorescence image, the method comprising:
receiving, by an image analysis system, a digital image of a slide, the slide comprising the tissue sample, a target dot and a fluoro dot, the fluoro dot comprising a known density of fluorescence-inducing molecules, the target dot comprising a known density of target molecules, the tissue sample and the target dot having been stained in the same staining procedure with the same type of fluorescence-inducing molecules as contained in the fluoro dot, the digital image comprising intensity values of the tissue sample, intensity values of the target dot and intensity values of the fluoro dot, the fluorescence-inducing molecules being adapted to directly or indirectly bind to the target molecules during the staining procedure;
receiving, by the image analysis system:
pixel intensities of the fluoro dot depicted in the image;
pixel intensities of the target dot depicted in the image;
pixel intensities of an area of the tissue sample depicted in the image;
fluorescence-inducing molecule density information indicative of the known density of the fluorescence-inducing molecules in the fluoro dot; and
target molecule density information indicative of the known density of the target molecules in the target dot; and
computing the density of target molecules in the area of the tissue sample as a function of the pixel intensities of the fluoro dot, the target dot, the area of the tissue sample, the fluorescence-inducing molecule density information and the target molecule density information.

2. The image analysis method of claim 1, the computation of the density of the target molecules in the tissue area comprising:
computing the average intensity $I_{FID\_AVG}$ of the pixel intensities of the fluoro dot according to:

$$I_{FID\_AVG} = \frac{\sum I_{px\_FD}}{\#\text{pixel in } FD}$$

computing the average intensity $I_{TaD\_AVG}$ of the pixel intensities of the target dot according to:

$$I_{TaD\_AVG} = \frac{\sum I_{px\_TaD}}{\#\text{pixel in } TaD}$$

computing the ratio R of fluorescence-inducing molecules per target molecule in the target dot according to:

$$R = \frac{I_{TaD\_AVG}}{I_{FID\_AVG}};$$

computing the density $\delta_{Target\_in\_Tissue}$ of the target molecules in the area of the tissue sample according to:

$$\delta_{Target\_In\_Tissue} = \frac{\frac{I_{TaD\_AVG}}{\mu m\ 2\ \text{tissue area}}}{\frac{I_{FID\_AVG}}{\mu m\ 2\ \text{target dot}}} \times \delta_{Target\_In\_Target\_dot} \times R,$$

wherein $\delta_{Target\_In\_Target\_dot}$ is the density of target molecules in the target dot.

3. The image analysis method of claim 1, further comprising:
coating an area of the slide with the target molecules, thereby creating the target dot.

4. The image analysis method of claim 3, the coating of the area of the slide being performed using protein microarray technology.

5. The image analysis method of claim 1, further comprising generating the target dot, the generation comprising:

attaching reference cells homogeneously to an area of the slide, thereby generating the target dot, the reference cells expressing or comprising a known number of the target molecules.

6. The image analysis method of claim 5, the method further comprising, before the attaching of the reference cells is performed:
Before the attaching of the reference cells is performed, experimentally determining the average number of the target molecules which are expressed in or are contained in a set of reference cells; and
counting the number of cells attached to the target dot.

7. The image analysis method of claim 6, the experimental determination comprising:
Processing a reference tissue sample, in particular a FFPE tissue sample, for transforming the reference tissue sample into a homogeneous suspension of reference cells;
Experimentally determining the average number of target molecules comprised in the reference cells in the suspension or in a sub-set of the reference cells in the suspension.

8. The image analysis method of claim 1, the experimental determination comprising performing a mass spectroscopy analysis or performing a flow cytometry analysis for a quantitative determination of target molecules in the reference cells.

9. The image analysis method of claim 1, wherein the ratio of fluorescence-inducing molecules that bind to a single target molecule during the staining procedure is unknown and depends on one or more parameters of the staining protocol.

10. The image analysis method of claim 1, wherein the staining protocol is a tyramide signal amplification staining protocol.

11. The image analysis method of claim 1, the binding of a fluorescence-inducing molecule to a single target molecule being selected from a group comprising:
a covalent or ionic binding to the target molecule or to one or more intermediary molecules connected with the target molecule;
dipole-dipole interactions, Van-der-Waals interactions or hydrogen binding to the target molecule or one or more intermediary molecules connected with the target molecule;
an antigen-antibody binding;
a hybridization of nucleic acid sequences.

12. The image analysis method of claim 1, the fluorescence-inducing molecules being fluorophores or enzymes that trigger the emission of fluorescence signals by other molecules in spatial proximity to the fluorescence-inducing molecules.

13. The image analysis method of claim 1, the fluoro dot comprising a known density of further fluorescence-inducing molecules of at least one further type of fluorescence-inducing molecules, the tissue sample and the target dot both having been stained in addition with the further fluorescence-inducing molecules, the method comprising:
Receiving a further digital image of the slide, the further digital image comprising intensity values of the tissue sample, intensity values of the target dot and intensity values of the fluoro dot, the intensity values of the fluoro dot, the target dot and the tissue sample correlating with the number of the further fluorescence-inducing molecules in the fluoro dot, the target dot and the tissue dot, the further fluorescence-inducing molecules being adapted to directly or indirectly bind to the target molecules during the staining procedure;
receiving:
further pixel intensities of the fluoro dot depicted in the further image;
further pixel intensities of the target dot depicted in the further image;
further pixel intensities of the area of the tissue sample depicted in the further image;
further fluorescence-inducing molecule density information indicative of the known density of the further fluorescence-inducing molecules in the fluoro dot;
computing a further density of target molecules in the area of the tissue sample as a function of the further pixel intensities of the fluoro dot, the target dot, the area of the tissue sample, the further density information of the further fluorescence-inducing molecules and the target molecule density information.

14. The image analysis method of claim 1, the target molecule being selected from a group comprising:
a biomarker molecule;
a primary antibody capable of selectively binding to the biomarker molecule in a predefined molecular ratio;
a secondary antibody capable of selectively binding to the primary antibody in a predefined molecular ratio.

15. An image analysis system configured for determining the density of target molecules in a tissue sample depicted in a fluorescence image, the system comprising a storage medium and one or more processors configured for:
receiving a digital image of a slide, the slide comprising the tissue sample, a target dot and a fluoro dot, the fluoro dot comprising a known density of fluorescence-inducing molecules, the target dot comprising a known density of target molecules, the tissue sample and the target dot having been stained in the same staining procedure with the same type of fluorescence-inducing molecules as contained in the fluoro dot, the digital image comprising intensity values of the tissue sample, intensity values of the target dot and intensity values of the fluoro dot, the fluorescence-inducing molecules being adapted to directly or indirectly bind to the target molecules during the staining procedure;
receiving:
pixel intensities of the fluoro dot depicted in the image;
pixel intensities of the target dot depicted in the image;
pixel intensities of an area of the tissue sample depicted in the image; and
fluorescence-inducing molecule density information indicative of the known density of the fluorescence-inducing molecules in the fluoro dot;
target molecule density information indicative of the known density of the target molecules in the target dot; and
computing the density of target molecules in the area of the tissue sample as a function of the received pixel intensities of the fluoro dot, the target dot, the area of the tissue sample, the fluorescence-inducing molecule density information and the target molecule density information.

16. A slide comprising a tissue sample, a target dot and a fluoro dot, the fluoro dot comprising a known density of fluorescence-inducing molecules, the target dot comprising a known density of target molecules.

17. The slide of claim 16, the slide with the tissue sample and the target dot having been stained in the same staining procedure with the same type of fluorescence-inducing molecule as contained in the fluoro dot, the fluorescence-inducing molecules being adapted to directly or indirectly bind to the target molecules during the staining procedure.

18. The slide of claim 16, the fluoro dot of the slide comprising a known density of further fluorescence-inducing molecules of at least one further type of fluorescence-inducing molecules, the further fluorescence-inducing molecules being adapted to directly or indirectly bind to the target molecules during the staining procedure.

19. The slide of claim 16, the target dot being an area of the slide that is coated with a known number of the target molecules or that is coated with a known number of cells, the cells expressing or comprising a known number of the target molecules.

\* \* \* \* \*